United States Patent

Feyh et al.

(10) Patent No.: US 9,588,073 B2
(45) Date of Patent: Mar. 7, 2017

(54) RESISTIVE MEMS HUMIDITY SENSOR

(71) Applicant: Robert Bosch GmbH, Stuttgart (DE)

(72) Inventors: Ando Feyh, Palo Alto, CA (US); Andrew Graham, Redwood City, CA (US); Ashwin Samarao, Mountain View, CA (US); Gary Yama, Mountain View, CA (US); Gary O'Brien, Palo Alto, CA (US)

(73) Assignee: Robert Bosch GmbH, Stuttgart (DE)

( * ) Notice: Subject to any disclaimer, the term of this patent is extended or adjusted under 35 U.S.C. 154(b) by 132 days.

(21) Appl. No.: 14/108,198

(22) Filed: Dec. 16, 2013

(65) Prior Publication Data

US 2014/0167791 A1    Jun. 19, 2014

Related U.S. Application Data

(60) Provisional application No. 61/739,633, filed on Dec. 19, 2012.

(51) Int. Cl.
*G01N 27/12* (2006.01)

(52) U.S. Cl.
CPC .................... *G01N 27/121* (2013.01)

(58) Field of Classification Search
USPC .............. 324/694, 664, 689, 693; 73/335.05, 73/29.01, 31.01, 335.02, 73;
(Continued)

(56) References Cited

U.S. PATENT DOCUMENTS

| 4,156,268 A | 5/1979 | Gallant |
| 4,263,576 A * | 4/1981 | Murata et al. ............ 338/35 |

(Continued)

FOREIGN PATENT DOCUMENTS

DE    102007047156 A1    4/2009

OTHER PUBLICATIONS

Wong et al., Espacenet Translation, Humidity sensor for detecting amount of water in e.g. liquid, has physical transducer coupled with sensor layer in such manner that characteristic of transducer depends on water amount absorbed by sensor layer, Apr. 23, 2009.*

(Continued)

*Primary Examiner* — Melissa Koval
*Assistant Examiner* — Nasima Monsur
(74) *Attorney, Agent, or Firm* — Maginot Moore & Beck LLP

(57) ABSTRACT

A semiconductor device includes a substrate, an insulating film provided on a surface of the substrate, and a sensing film formed of a conductive material deposited on top of the insulating film. The sensing film defines at least one conductive path between a first position and a second position on the insulating film. A first circuit connection is electrically connected to the sensing film at the first position on the insulating layer, and a second circuit connection is electrically connected to the sensing film at the second position. A control circuit is operatively connected to the first circuit connection and the second circuit connection for measuring an electrical resistance of the sensing film. The sensing film has a thickness that enables a resistivity of the sensing film to be altered predictably in a manner that is dependent on ambient moisture content.

12 Claims, 3 Drawing Sheets

(58) Field of Classification Search
USPC ....... 257/E21.602, E29.166, 288; 438/49, 53
See application file for complete search history.

(56) References Cited

U.S. PATENT DOCUMENTS

| | | | |
|---|---|---|---|
| 4,928,513 A * | 5/1990 | Sugihara et al. | ............ 73/25.03 |
| 5,036,704 A | 8/1991 | Pusatcioglu et al. | |
| 7,193,290 B2 | 3/2007 | Benzel et al. | |
| 7,426,067 B1 | 9/2008 | Bright et al. | |
| 8,003,513 B2 * | 8/2011 | Shah et al. | ................... 438/622 |
| 8,132,457 B2 | 3/2012 | Haji-Sheikh et al. | |
| 2008/0221806 A1 * | 9/2008 | Bryant et al. | ................... 702/22 |
| 2010/0307238 A1 | 12/2010 | Van Popta et al. | |

OTHER PUBLICATIONS

International Search Report and Written Opinion corresponding to PCT Application No. PCT/US2013/075677, mailed Mar. 24, 2014 (15 pages).

Yoo, Kum-Pyo et al., Novel Resistive-Type Humidity Sensor based on Multiwall Carbon Nanotube/polyimide Composite Films, Sensors and Actuators B: Chemical: International Journal Devoted to Research and Development of Physical and Chemical Transducers, Elsevier S.A, CH, vol. 145, No. 1, Mar. 4, 2010 (6 pages).

* cited by examiner

RESISTIVE MEMS HUMIDITY SENSOR

CROSS-REFERENCE TO RELATED APPLICATIONS

This application claims priority to U.S. Provisional Application Ser. No. 61/739,633 entitled "RESISTIVE MEMS HUMIDITY SENSOR" by Feyh et al., filed Dec. 19, 2012, the disclosure of which is hereby incorporated herein by reference in its entirety.

TECHNICAL FIELD

This disclosure relates generally to semiconductor devices and particularly to microelectromechanical system (MEMS) humidity sensors.

BACKGROUND

Humidity sensors are widely used in various fields to measure the amount of water vapor present in the air of a particular environment. Humidity sensors are configured as capacitive sensor devices that use capacitance to measure humidity. Capacitive humidity sensors include a dielectric layer interposed between a pair of electrodes. The dielectric layer is formed of a material, such as polymer, that is configured to absorb and retain water molecules at concentrations that are proportional to the ambient humidity. The water molecules alter the capacitance between the two electrodes in a manner that depends on concentration. Humidity can therefore be determined by measuring the capacitance between the two electrodes and correlating the measured capacitance to a corresponding humidity value.

While effective in measuring humidity, capacitive humidity sensors rely on bulk effects to alter capacitance and indicate changes in humidity. As a result, capacitive humidity sensors typically have a relatively slow response time to changes in ambient humidity. This is because it takes time for the water molecules to diffuse into and out of the dielectric layer of the sensor in response to changes in humidity. To avoid time-lag errors, capacitive humidity sensors require a long time constant to allow the water concentration in the dielectric layer to reach equilibrium before capacitance measurements are performed.

Capacitive humidity sensors are also susceptible to drift and damage as a result of contamination and/or aging. For example, as water molecules are absorbed into and released from the dielectric layer, non-water molecules can be absorbed into the dielectric material absorbed into the dielectric material along with the water molecules. In some cases, the non-water molecules can become trapped in the dielectric material. Over time, the buildup of non-water molecules, or contamination, in the dielectric can alter the capacitance response of the sensor and/or reduce the ability of the dielectric material to absorb water molecules.

DRAWINGS

DESCRIPTION

Figure 1A:
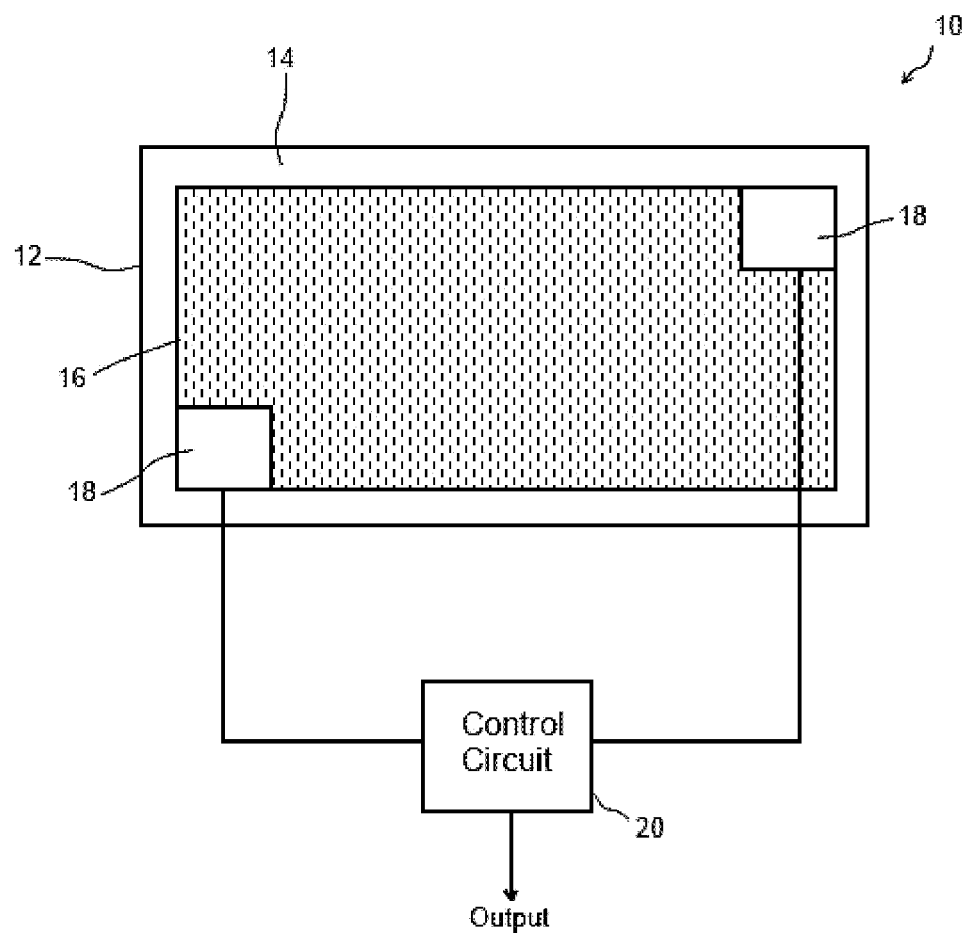
FIG. 1A is a schematic view of an embodiment of a resistive MEMS humidity sensor in accordance with the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one of ordinary skill in the art to which this disclosure pertains.

In one embodiment of the disclosure, a semiconductor device includes a substrate, an insulating film provided on a surface of the substrate, and a sensing film formed of a conductive material deposited on top of the insulating film. The sensing film defines at least one conductive path between a first position and a second position on the insulating film. A first circuit connection is electrically connected to the sensing film at the first position on the insulating layer, and a second circuit connection is electrically connected to the sensing film at the second position. A control circuit is operatively connected to the first circuit connection and the second circuit connection for measuring an electrical resistance of the sensing film. The sensing film has a thickness that enables a resistivity of the sensing film to be altered predictably in a manner that is dependent on ambient moisture content.

The sensing film may have a thickness of approximately 1-10 nm and may be formed of a suitable conductive material, such as platinum, aluminum, titanium, titanium nitride, or tantalum nitride. The insulating film may have a thickness in a range from less than 10 nm to approximately 5 mm. The sensing film and the insulating film may be deposited using an atomic layer deposition (ALD) process.

In one embodiment, the sensing film is patterned to include a plurality of voids to reduce the conductivity of the sensing film. The voids may be used to absorb water molecules so as to alter the resistivity of the sensing film. The dielectric material of the insulating layer under the voids may comprise a hydrophobic material or a hydrophilic material to help water molecules collect in the voids, e.g., by pushing water away from the substrate into the voids or by drawing water from the film into the voids. The control circuit is configured to correlate the measured resistance of the sensing film to a humidity value. The control circuit may also be configured to pass a reset pulse through the sensing film. The reset pulse is configured to heat the sensing film to a degree that causes water molecules to be desorbed from the sensing film.

A method of fabricating a semiconductor device is also provided. The method comprises depositing a dielectric material onto a surface of a substrate to form an insulating film, and depositing a conductive sensing film on top of the insulating film to form a conductive path between a first position and a second position on the insulating film. The sensing film is deposited to a thickness that enables a resistivity of the sensing film to be altered in a manner that is dependent on ambient moisture content. A first circuit connection is formed at the first position, and a second circuit connection is formed at the second position.

In addition, a method of operating a humidity sensor is provided. The method comprises passing a measuring current through a conductive sensing film of the humidity sensor, the sensing film being deposited on top of a dielectric insulating film provided on a substrate and having a thickness of approximately 1-10 nm such that a resistivity of the sensing film is altered in a manner that is dependent on ambient moisture content. The measuring current is then evaluated to determine an electrical resistance of the sensing film. The determined resistance is then correlated to a humidity value.

Figure 1B:
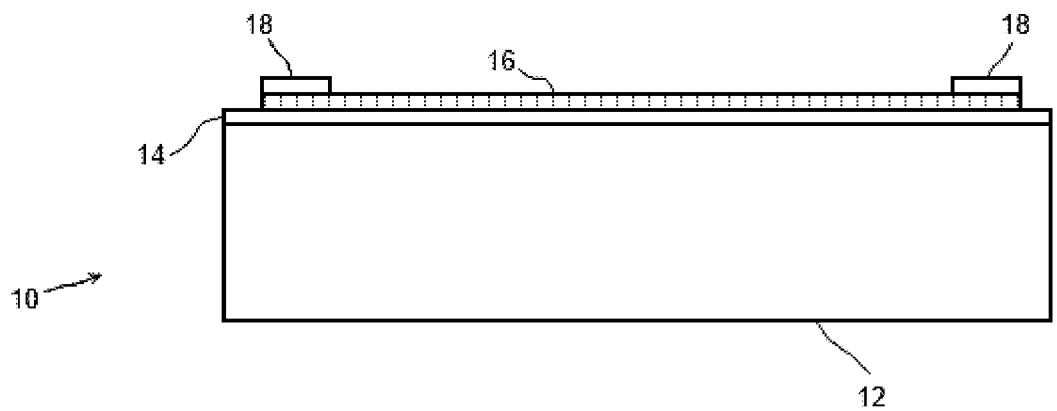
FIG. 1B is a cross-sectional view of the resistive MEMS humidity sensor of FIG. 1A.

FIGS. 1A and 1B depict a schematic view of an embodiment of a resistive MEMS humidity sensor 10 in accordance with the present disclosure. The humidity sensor 10 includes a substrate 12, an insulating film 14, a sensing film 16, and a pair of bonding pads or connection terminals 18. The substrate 12 may comprise a complementary metal oxide semiconductor (CMOS) substrate, which in one embodiment is a silicon wafer, or on another type of substrate. Although not depicted, the humidity sensor 10 in accordance with this disclosure may be easily integrated onto other sensor devices, such as pressure sensors or microphones.

The insulating film 14 of the humidity sensor 10 comprises a layer of dielectric material deposited on the substrate 12. The insulating film 14 is formed of a suitable dielectric material such as aluminum oxide (Al2O3), silicon dioxide (SiO2), silicon mononitride (SiN), trisilicon tetranitride (Si3N4), silicon carbide (SiC), and the like. In one embodiment, the insulating film has a thickness that is between less than 10 nm thick to approximately 5 mm (<10 nm to 5 mm). The insulating film 14 may be deposited in any suitable manner that allows the desired film thickness.

The sensing film 16 comprises a metal or semiconductor film deposited onto the insulating film 14. Examples of materials that may be used for the sensing film include platinum (Pt), aluminum (Al), titanium (Ti), and titanium nitride (TiN), tantalum nitride (TaN), and the like, although other suitable metal or semiconductor materials may be used. The bonding pads 18 are provided to connect the sensing film 16 to control circuitry 20. The control circuitry 20 is configured to pass a known current through the sensing film and to measure changes in electrical resistance, or impedance, in the sensing film that are caused by changes in the moisture content of the air.

The sensing film 16 is configured to form a resistive circuit element between the bonding pads 18 with an electrical resistance that varies with humidity. The sensing film 16 may be configured to have a resistance value that is approximately 10-10000 ohms/square. In one embodiment, the sensing film is deposited at a thickness of approximately 1-10 nm using an atomic layer deposition (ALD) process. ALD is a deposition technique that uses sequential, self-limiting surface reactions to deposit thin films one atomic layer at a time. This allows very thin films to be formed with precise and uniform thickness. Thinner sensing films are typically preferred because they have a higher intrinsic resistance that can be more easily influenced by changes in water vapor concentration than thicker sensing films.

Because the sensing film 16 is very thin (e.g., 1-10 nm), the changes in the electrical resistance of the film are primarily the result of surface effects caused by water molecules altering conductivity at the surface of the film 16. The resistive humidity sensor 10 therefore can have a much smaller time-constant, and therefore a faster response time, than conventional capacitive humidity sensors that utilize bulk effect. In addition, by utilizing a surface effect, the sensing film 16 is less susceptible to errors and drift resulting from bulk contamination and aging.

Figure 2:
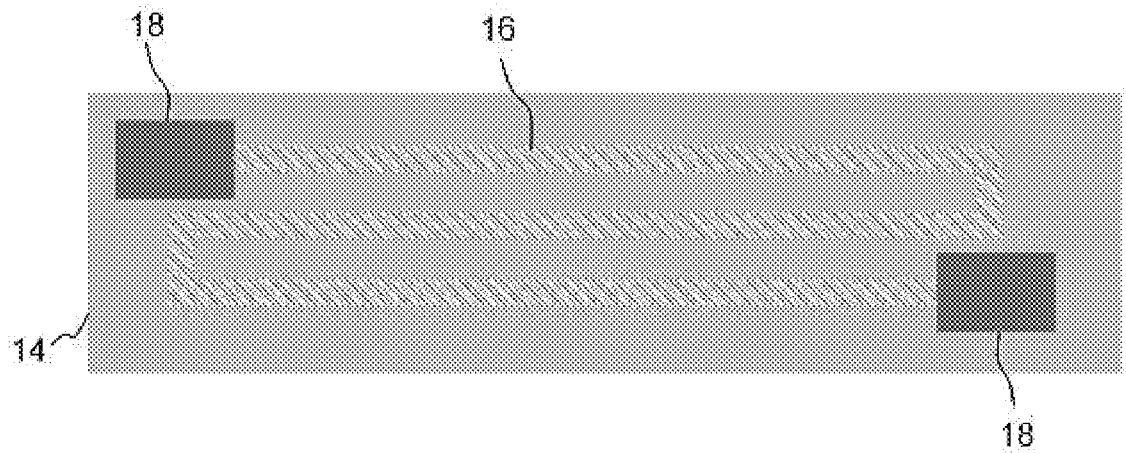
FIG. 2 is a top elevational view of an embodiment of the sensor of FIG. 1 showing a sensing film having a meandering pattern.

The sensing film 16 may be patterned or shaped in a manner that increases the intrinsic resistance of the sensing element and/or that increases the sensitivity of the resistance of the film to changes in humidity. In one embodiment, the sensing film 16 is patterned to form a mesh, grid, or array like structure, such as depicted in FIGS. 1A and 1B. The sensing film 16 may be patterned to form other shapes, such as a serpentine shape, as depicted in FIG. 2, which follows a meandering path between the bonding pads 18.

Figure 3:
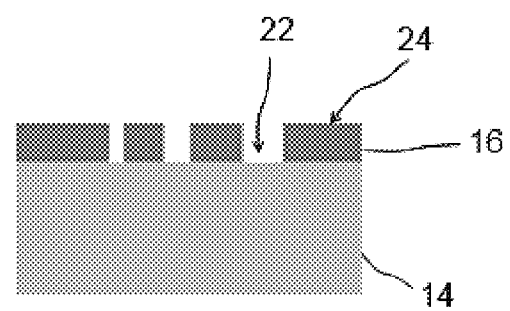
FIG. 3 is a cross-sectional view of the insulating film and sensing film of FIGS. 1 and 2 showing the absorption sites of the sensor.

The patterning of the sensing film 16 results in the sensing film 16 having openings, pores, or gaps 22, referred to herein as voids, located between the sections, segments, or strips 24 of the sensing film 16 as depicted in FIG. 3. In porous sensing films, there are primarily two types of absorption sites for water vapor. One type of absorption site is on the sections, segments, or strips 24 of the sensing film 16. The other type of absorption site is on the insulating film 14 in the voids 22 between the strips 24. The dielectric material used for the insulating layer can be selected to enhance the ability of one or both of the absorption sites to absorb water molecules and add conductivity paths along the sensing film 16 between the bonding pads.

As examples, the dielectric material may comprise one of a hydrophobic material and a hydrophilic material. When the dielectric is hydrophilic, water molecules will be drawn toward the insulating film 14 and adsorb on the sites located in the voids 22 between the strips 24 of the sensing film 16. When the dielectric is hydrophobic, water molecules will be pushed away from the insulating film 14 toward the absorption sites on the strips 24 of the sensing film. In both ways, the resistance of the porous sensor film 16 is reduced as the water molecules add conductivity paths across the sensing film 16 between the bonding pads 18.

In an alternative embodiment, the materials for the dielectric and the sensing film may be provided such that the absorption sites in the voids 22 and on the strips 24 have comparable absorption strength. In another alternative embodiment, the sensing film 16 may be provided as a substantially contiguous layer (not shown) that is non-porous. In this embodiment, the water molecules will absorb only onto the surface of the sensing film 16 to provide additional conductivity paths.

The bond pads 18 are connected to the control circuitry 20 for monitoring the resistance, or impedance, of the sensing film 16 between the bonding pads 18. The control circuitry 20 may be configured to measure the resistance, or impedance, in any suitable manner. For example, in one embodiment, the control circuitry 20 is configured to pass a known current pulse through the sensing film 16 via the bonding pads 18 and measure the voltage drop across the sensing film 16. The control circuitry 20 may be configured to generate current pulses at various current levels and various durations for measuring the resistance of the sensing film 16. In one embodiment, the control circuitry is configured to output a signal that is indicative of the electrical resistance of the sensing film 16. The control circuitry 20 may be configured to process the measured resistance value to determine the corresponding humidity. Alternatively, the output signal from the control circuit 20 may be correlated to a humidity value by an external circuit.

The use of a thin sensing film 16 as described above enables a reset protocol to be implemented in the sensor to reduce the amount of time required for the sensor 10 to respond to changes in humidity. For example, the thin sensing film 16 can be reset by passing a current pulse at a suitably high level of current through the sensing film 16 to cause the sensing film 16 to heat up. When the sensing film 16 is heated up to a sufficient degree, the water molecules absorbed into and on the sensing film 16 will be efficiently and quickly desorbed. The use of such a reset pulse can reduce drift effects due to, for example, particle or ionic contamination. Such a heating pulse can be programmed to be performed at regularly scheduled intervals, under predetermined conditions, or on an as needed basis. The heating pulse can also be used as a reset to determine the current sensor baseline. Such a reset pulse may be configured for actuation manually through a user interface of the sensor device 10. As an alternative to the use of the heating pulse for resetting the sensing film 16, the sensor 10 may be provided with a heating structure (not shown), such as a resistive film, below the sensing film 16 that is configured to heat the sensing film 16 and cause the desorption of water from the film 16.

Figure 4:
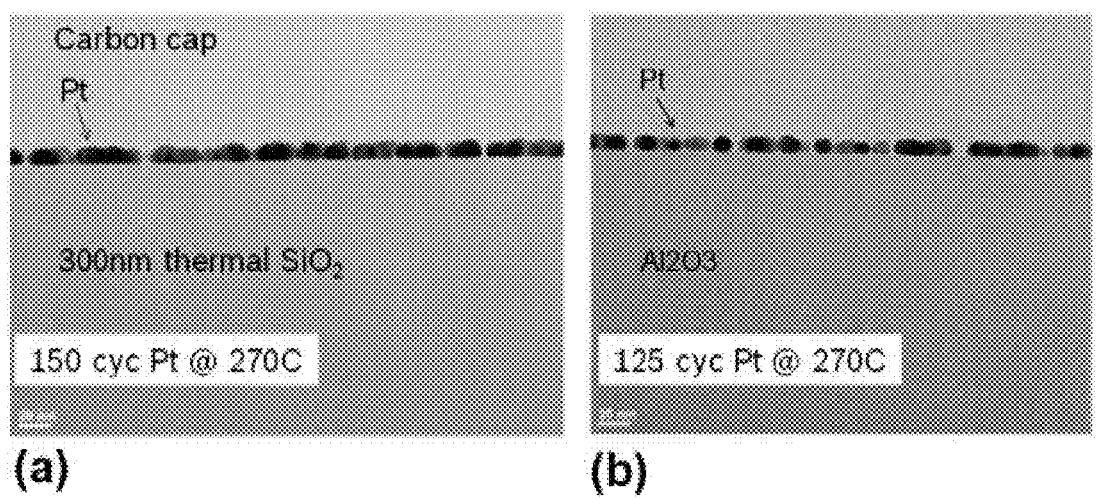
FIGS. 4A and 4B are depictions of sensing films for resistive MEMS humidity sensors being formed in situ.

In an alternative embodiment, a film 16, such as depicted in FIG. 3, can be formed as a porous layer in situ. For example, referring to FIG. 4, a thin platinum (Pt) film deposited using ALD can exhibit high porosity on certain types of surface materials. FIG. 4(a) depicts an exemplary embodiment showing a platinum (Pt) film deposited on a thermal silicon dioxide ($SiO_2$) having thickness of 300 nm. The Pt film is deposited on the thermal $SiO_2$ by ALD with 150 cycles at 270° C. In FIG. 4(a), the $SiO_2$ serves as a seed layer for the Pt deposition. To enable Plasma Enhanced ALD (PE-ALD), another type of seed layer is used as $SiO_2$ is generally not usable as seeding for Pt in PE-ALD. For example, FIG. 4(b) depicts a Pt film deposited using a PE-ALD process onto an aluminum oxide ($Al_2O_3$) which serves as the seed layer for Pt during the PE-ALD. In FIG. 4(b), the Pt film is deposited on the $Al_2O_3$ by PE-ALD with 125 cycles at 270° C.

In other alternative embodiments, the film 16 may be provided with various configurations to realize different types of resistor structures and circuits. For example, in one embodiment (not shown), the film 16 may be provided in the form of a half Wheatstone-bridge circuit to facilitate read out and evaluation of the sensor. In some embodiments, resistor structures in addition to film 16 may be incorporated into the sensor 10 to implement additional sensor elements. For example, in one embodiment, an additional resistor structure (not shown) similar in configuration to film 16 may be provided in the sensor 10 with a protective coating to reduce or eliminate sensitivity to humidity effects in order to serve as a reference element for the sensor. In another embodiment, an additional resistor structure may be included in the sensor 10 to implement a thermistor for temperature measurement.

In yet another embodiment (not shown), a porous metal, such as platinum, comprising Pt nano-crystallites is provided between two solid metal electrodes to form an interdigitated electrode configuration (e.g., similar to interlocked fingers of two clasped hands). In this embodiment, water molecules will be absorbed by the porous metal resulting in changes in the effective resistance or capacitance between the two electrodes. Humidity measurements can be made by detecting changes in insulation resistance/capacitance between the two electrodes.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A semiconductor device comprising:
  a substrate;
  an insulating film formed of a dielectric material and provided on a surface of the substrate;
  a sensing film formed of a conductive material deposited on top of the insulating film, the sensing film defining at least one conductive path between a first position and a second position on the insulating film;
  a first circuit connection electrically connected to the sensing film at the first position on the insulating layer;
  a second circuit connection electrically connected to the sensing film at the second position; and
  a control circuit operatively connected to the first circuit connection and the second circuit connection and configured to measure an electrical resistance of the sensing film,
  wherein the sensing film has a thickness that enables a resistivity of the sensing film to be altered predictably in a manner that is dependent on ambient moisture content, and
  wherein the control circuit is configured to pass a reset pulse through the sensing film via the first and the second circuit connections, the reset pulse being configured to heat the sensing film to a degree that causes water molecules to be desorbed from the sensing film.

2. The device of claim 1, wherein the sensing film has a thickness approximately 1-10 nm.

3. The device of claim 2, wherein the sensing film comprises platinum, aluminum, titanium, titanium nitride, or tantalum nitride.

4. The device of claim 2, wherein the sensing film is deposited using an atomic layer deposition (ALD) process.

5. The device of claim 2, wherein the insulating film has a thickness in a range from less than 10 nm to approximately 5 mm.

6. The device of claim 2, wherein the sensing film is patterned to include a plurality of voids between the first and the second positions extending down to the insulating layer that reduce the conductivity of the sensing film.

7. The device of claim 6, wherein the plurality of voids cause the sensing film to have a serpentine shape.

8. The device of claim 6, wherein the plurality of voids cause the sensing film to be porous.

9. The device of claim 6, wherein the voids are configured to absorb water molecules, and
  wherein the water molecules absorbed in the voids alter the resistivity of the sensing film.

10. The device of claim 9, wherein the dielectric material of the insulating layer under the voids comprises one of a hydrophobic material and a hydrophilic material.

11. The device of claim 1, wherein the control circuit is configured to correlate the measured resistance of the sensing film to a humidity value.

12. A method of operating a humidity sensor, the method comprising:
  passing a measuring current through a conductive sensing film of the humidity sensor, the sensing film being deposited on top of a dielectric insulating film provided on a substrate and having a thickness of approximately 1-10 nm such that a resistivity of the sensing film is altered in a manner that is dependent on ambient moisture content;
  evaluating the measuring current to determine an electrical resistance of the sensing film; and correlating the determined resistance to a humidity value; and passing a reset current through the sensing film to heat the sensing film to a degree that causes water molecules to be desorbed from the sensing film.

\* \* \* \* \*